(12) United States Patent
Freeman et al.

(10) Patent No.: US 11,813,084 B2
(45) Date of Patent: *Nov. 14, 2023

(54) MEASURING MYOCARDIAL PHYSIOLOGIC PARAMETERS

(71) Applicant: Zoll Medical Corporation, Chelmsford, MA (US)

(72) Inventors: Gary A. Freeman, Waltham, MA (US); Ulrich Herken, Medford, MA (US); Christopher Kaufman, Somerville, MA (US); Annemarie Elizabeth Silver, Bedford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 161 days.

This patent is subject to a terminal disclaimer.

(21) Appl. No.: 17/350,730

(22) Filed: Jun. 17, 2021

(65) Prior Publication Data

US 2022/0039746 A1 Feb. 10, 2022

Related U.S. Application Data

(63) Continuation of application No. 16/369,604, filed on Mar. 29, 2019, now Pat. No. 11,058,356, which is a continuation of application No. 14/926,473, filed on Oct. 29, 2015, now Pat. No. 10,278,646.

(60) Provisional application No. 62/072,319, filed on Oct. 29, 2014.

(51) Int. Cl.
*A61B 5/00* (2006.01)
*A61B 5/02* (2006.01)
(Continued)

(52) U.S. Cl.
CPC ............ *A61B 5/684* (2013.01); *A61B 5/0075* (2013.01); *A61B 5/02* (2013.01); *A61B 5/14539* (2013.01);
(Continued)

(58) Field of Classification Search
CPC ......... A61B 5/684; A61B 5/0075; A61B 5/02; A61B 5/14539; A61B 5/6823;
(Continued)

(56) References Cited

U.S. PATENT DOCUMENTS

| 5,497,769 A | 3/1996 | Gratton |
| 10,278,646 B2 | 5/2019 | Freeman et al. |

(Continued)

OTHER PUBLICATIONS

PCT International Search Report and Written Opinion issued in International Appln. No. PCT/US2015/057993, dated Feb. 26, 2016, 14 pages.

*Primary Examiner* — Mark W. Bockelman
(74) *Attorney, Agent, or Firm* — Fish & Richardson P.C.

(57) ABSTRACT

A method for measuring a myocardial physiologic parameter according to an embodiment includes placing an at least partially convex portion of a spectral sensor against an intercostal space of a human over a heart of the human and measuring the physiologic parameter of a myocardium of the heart with the spectral sensor over time during an emergency medical event. The spectral sensor may be configured to determine and visually display a suggested position adjustment for directing the spectral radiation more directly toward the tissue of interest (e.g. the myocardium), and/or for placing the operative elements of the spectral sensor closer to the tissue of interest (e.g. the myocardium).

20 Claims, 13 Drawing Sheets

(51) Int. Cl.
*A61N 1/04* (2006.01)
*A61B 5/145* (2006.01)
*A61B 5/318* (2021.01)

(52) U.S. Cl.
CPC .......... *A61B 5/6823* (2013.01); *A61B 5/7246* (2013.01); *A61B 5/742* (2013.01); *A61B 5/7405* (2013.01); *A61B 5/7455* (2013.01); *A61N 1/046* (2013.01); *A61B 5/318* (2021.01); *A61B 2560/0425* (2013.01); *A61B 2562/0219* (2013.01)

(58) Field of Classification Search
CPC ..... A61B 5/7246; A61B 5/7405; A61B 5/742; A61B 5/7455; A61B 5/318; A61B 2560/0425; A61B 2562/0219; A61N 1/046
See application file for complete search history.

(56) References Cited

U.S. PATENT DOCUMENTS

| | | |
|---|---|---|
| 11,058,356 B2 | 7/2021 | Freeman et al. |
| 2005/0033177 A1 | 2/2005 | Rogers |
| 2007/0038041 A1 | 2/2007 | Yang |
| 2010/0049052 A1 | 2/2010 | Sharf |
| 2011/0205535 A1 | 8/2011 | Soller |
| 2014/0135666 A1 | 5/2014 | Butler |
| 2016/0120469 A1 | 5/2016 | Freeman et al. |
| 2019/0223794 A1 | 7/2019 | Freeman et al. |

MEASURING MYOCARDIAL PHYSIOLOGIC PARAMETERS

CROSS-REFERENCE TO RELATED APPLICATIONS

This application is a continuation of U.S. patent application Ser. No. 16/369,604, filed Mar. 29, 2019, which is a continuation of U.S. patent application Ser. No. 14/926,473, filed Oct. 29, 2015, which itself claims the benefit of U.S. Provisional Patent Application Ser. No. 62/072,319, filed on Oct. 29, 2014, which is incorporated herein by reference in its entirety for all purposes.

TECHNICAL FIELD

Embodiments of the present invention relate generally to spectral sensors for measuring physiologic parameters, and more specifically to spectral sensors for measuring myocardial physiologic parameters through an intercostal space.

BACKGROUND

Spectral sensors for noninvasive measurement or calculation of physiologic parameters (PP) such as, for example, oxygen saturation, oxygen tension, pH, hematocrit, hemoglobin concentration, anaerobic threshold, water content, and oxygen consumption, which are described in the art, for example in U.S. Patent Application Publication No. 2011/0205535, published Aug. 25, 2011 ("the '535 Publication"), the contents of which are incorporated by reference herein in their entirety for all purposes. One such spectral sensor 10 is illustrated in FIGS. 1 and 2, reproduced from the '535 Publication, which show a spectral detector 12, two short-distance radiation sources 14a, 14b, and six long-distance radiation sources 16a-16e. The housing 11 includes a concave inner surface that is configured for placement against a patient's skin above tissue, for example peripheral muscle tissue, which is to be monitored. The housing 11 further includes a handle 15 on each side, as well as apertures 17a, 17b for communications interface. As shown in FIG. 2, the radiation sources 14a, 14b and 16a-16e may be part of a circuit board 18.

However, spectral sensors such as sensor 10 often rely in general on their initial positioning over a larger muscle, for example a shoulder or arm muscle, without any indication or assistance in positioning based upon effectiveness of tissue illumination.

SUMMARY

In Example 1, a system for non-invasively measuring a physiologic status of a myocardium of a patient according to an embodiment of the present invention includes a probe having a housing, wherein the housing is shaped to conform to a general shape of an indentation of an intercostal space of the patient; an optical spectroscope, at least partially disposed within the housing, the optical spectroscope comprising at least one light source capable of emitting light at a range of wavelengths, a wavelength-sensitive sensor capable of detecting light intensity, at two or more distinct wavelengths, of light scattered and/or reflected by tissue of the myocardium; and a processor communicably coupled to a memory, the memory including instructions that, when executed by the processor, cause the processor to (1) receive light intensity measurements from the optical spectroscope, and (2) determine a first magnitude of effectiveness of the at least one light source in illuminating the tissue of the myocardium.

In Example 2, the system of Example 1, wherein the housing has a generally convex outer profile to facilitate maintaining substantially continuous surface contact between the housing and the intercostal space when the housing is rotated.

In Example 3, the system of Example 1, wherein the first magnitude of effectiveness is based on an effectiveness of the at least one light source in illuminating the tissue of the myocardium.

In Example 4, the system of Example 1, wherein the memory further includes instructions that, when executed by the processor, cause the processor to cause a first indication to be communicated to the user, wherein the first indication indicates the first magnitude of effectiveness.

In Example 5, the system of any of Examples 1-4, wherein the first indication is communicated using at least one of a visual display, an audio tone, a verbal communication, and a haptic vibration of the probe.

In Example 6, the system of any of Examples 1-5, wherein the memory further includes instructions that, when executed by the processor, cause the processor to determine a second magnitude of effectiveness of determining the physiologic status of the myocardium of the patient, and to cause a second indication to be provided to the user, wherein the second indication indicates which of the first and second magnitudes of effectiveness is larger.

In Example 7, the system of any of Examples 1-6, wherein the second indication is communicated using at least one of a visual display, an audio tone, a verbal communication, and a haptic vibration of the probe.

In Example 8, the system of any of Examples 1-7, wherein the probe contains at least one inertial sensor.

In Example 9, the system of any of Examples 1-8, wherein the memory further includes instructions that, when executed by the processor, cause the processor to calculate positional information associated with the first magnitude of effectiveness, and to direct the user to an optimal position using directional commands to the user.

In Example 10, the system of any of Examples 1-9, wherein the memory further includes instructions that, when executed by the processor, cause the processor to evaluate the first magnitude of effectiveness over a range of positions of the probe and to direct the user to the optimal position within the range of positions using directional commands to the user.

In Example 11, the system of any of Examples 1-10, wherein the directional commands comprise at least one of a visual display, an audio tone, a verbal communication, and a haptic vibration of the probe.

In Example 12, the system of any of Examples 1-11, wherein the inertial sensor comprises one or both of an accelerometer and a gyroscope.

In Example 13, the system of any of Examples 1-12, wherein the probe is incorporated into a self-adhesive electrode attached to the patient's chest.

In Example 14, the system of any of Examples 1-13, wherein the electrode is a defibrillation electrode.

In Example 15, the system of any of Examples 1-14, wherein the probe comprises conformable material.

In Example 16, the system of any of Examples 1-15, wherein the conformable material includes silicone.

In Example 17, the system of any of Examples 1-16, wherein the memory further includes instructions that, when executed by the processor, cause the processor to compare a spectra received by the wavelength-sensitive sensor against one or more stored representations of known spectra to identify a type of underlying tissue, wherein the type of underlying tissue comprises at least one of bone, fat and myocardium.

In Example 18, the system of any of Examples 1-17, wherein the memory further includes instructions that, when executed by the processor, cause the processor to estimate the first magnitude of effectiveness based on the comparison.

In Example 19, the system of any of Examples 1-18, wherein the processor is communicably coupled to an electrocardiogram (ECG) sensor configured to generate an ECG trace associated with the patient; the memory further includes instructions that, when executed by the processor, cause the processor to calculate a cross-correlation coefficient between the ECG trace and the received spectra; and the first magnitude of effectiveness is based on the cross-correlation coefficient.

In Example 20, the system of any of Examples 1-19, wherein the memory further includes instructions that, when executed by the processor, cause the processor to utilize a spectral fit technique to perform the comparison.

In Example 21, the system of any of Examples 1-20, wherein the spectral fit technique includes a chi-square fit technique.

In Example 22, a method for measuring a myocardial physiologic parameter according to an embodiment of the present invention includes placing a spectral sensor comprising at least one radiation source on a patient's skin in a first position in an intercostal space above the patient's myocardium, wherein at least a portion of the spectral sensor has a convex outer profile for placement against a concave profile of the intercostal space; determining a first magnitude of effectiveness of the spectral sensor in measuring the myocardial physiologic parameter in the first position; moving, rotating or rolling the spectral sensor from the first position to a second position in the intercostal space; determining a second magnitude of effectiveness of the spectral sensor in measuring the myocardial physiologic parameter in the second position; comparing the first magnitude with the second magnitude; and based on the comparison, visually indicating a direction of position adjustment of the spectral sensor to achieve more effective measurement of the myocardial physiologic parameter.

In Example 23, the method of any of Examples 1-22, wherein the at least one radiation source comprises two or more long-distance radiation sources, and one or more short-distance radiation sources; the spectral sensor comprises a spectral detector, wherein at least two of the two or more long-distance radiation sources and at least one of the one or more short-distance radiation sources is located on the spectral sensor at different distances from the spectral detector; and the method further comprises selecting a radiation source of the two or more long-distance radiation sources which most effectively illuminates tissue of the myocardium for determining a physiologic parameter of the tissue of the myocardium.

In Example 24, the method of any of Examples 1-23, wherein the housing has a convex outer profile.

In Example 25, the method of any of Examples 1-24, wherein the first magnitude of effectiveness and the second magnitude of effectiveness is based on an effectiveness of the at least one radiation source in illuminating the tissue of the myocardium when the spectral sensor is in the first position and the second position, respectively.

In Example 26, the method of any of Examples 1-25, wherein the intercostal space is the second left intercostal space.

In Example 27, the method of any of Examples 1-26, wherein the intercostal space is the third left intercostal space.

In Example 28, the method of any of Examples 1-27, wherein the intercostal space is the fourth left intercostal space.

In Example 29, the method of any of Examples 1-28, wherein the convex outer profile is at least a portion of a cylinder, and wherein rotating or rolling the spectral sensor comprises rotating the spectral sensor about a longitudinal axis of the cylinder while the spectral sensor remains in the intercostal space.

In Example 30, the method of any of Examples 1-29, wherein visually indicating the direction of position adjustment comprises visually indicating a direction of rotation of the spectral sensor to achieve more direct orientation of the at least one radiation source toward the tissue of the myocardium.

In Example 31, the method of any of Examples 1-30, wherein visually indicating the direction of position adjustment comprises visually indicating a direction of translation of the spectral sensor to achieve a closer proximity of the at least one radiation source to the tissue of the myocardium.

In Example 32, the method of any of Examples 1-31, wherein visually indicating the direction of position adjustment comprises illuminating at least one light visible on the spectral sensor when the spectral sensor is placed against the skin in the intercostal space.

In Example 33, the method of any of Examples 1-32, further comprising providing haptic feedback to further indicate the direction of position adjustment.

In Example 34, the method of any of Examples 1-33, further comprising measuring the physiologic parameter of the myocardium.

In Example 35, the method of any of Examples 1-34, further comprising attaching the spectral sensor to the intercostal space and measuring the physiologic parameter of the myocardium over time.

In Example 36, the method of any of Examples 1-25, further comprising measuring the physiologic parameter of the myocardium over a first period of time when the spectral sensor is in the first position; calculating a first cross-correlation coefficient between a first electrocardiogram (ECG) trace taken during the first period of time and the measured physiologic parameter when the spectral sensor is in the first position, wherein the first magnitude of effectiveness is based on the first cross-correlation coefficient; measuring the physiologic parameter of the myocardium over a second period of time when the spectral sensor is in the second position; and calculating a second cross-correlation coefficient between a second ECG trace taken during the second period of time and the measured physiologic parameter when the spectral sensor is in the second position, wherein the second magnitude of effectiveness is based on the second cross-correlation coefficient.

In Example 27, a spectral sensor for measuring a myocardial physiologic parameter according to an embodiment of the present invention includes at least one radiation source; a spectral detector, a housing shaped for placement against a concave profile of an intercostal space; a visual indicator; and a processor communicably coupled to the at least one radiation source, the spectral detector, and the visual indicator, wherein, when the housing is placed against the concave profile of the intercostal space, the processor is configured to evaluate an effectiveness with which the spectral sensor can determine a physiologic parameter of the underlying myocardial tissue, at various positions of the spectral detector with respect to the intercostal space, and wherein the processor is further configured to, based on the evaluation of the effectiveness, activate the visual indicator so as to indicate a direction of position adjustment of the spectral sensor to achieve more effective determination of the physiologic parameter of the underlying myocardial tissue.

In Example 38, the spectral sensor of any of Examples 1-37, wherein the at least one radiation source comprises two or more long-distance radiation sources and one or more short-distance radiation sources, and wherein at least two of the two or more long-distance radiation sources and at least one of the one or more short-distance radiation sources are located on the spectral sensor at different distances from the spectral detector.

In Example 39, the spectral sensor of any of Examples 1-38, wherein the housing comprises a convex outer profile.

In Example 40, the spectral sensor of any of Examples 1-39, wherein the processor is configured to evaluate the effectiveness with which the spectral sensor can determine a physiologic parameter of the underlying myocardial tissue based on an effectiveness with which the at least one radiation source illuminates the underlying myocardial tissue.

In Example 41, the spectral sensor of any of Examples 1-40, wherein the processor is further configured to receive an electrocardiogram (ECG) trace from an ECG sensor, and a spectra signal from the spectral detector; and calculate a cross-correlation coefficient between the ECG trace and the spectra signal, wherein the effectiveness with which the spectral sensor can determine a physiologic parameter of the underlying myocardial tissue is based on the cross-correlation coefficient.

In Example 42, the spectral sensor of any of Examples 1-41, wherein the convex outer profile is at least a portion of a cylinder.

In Example 43, the spectral sensor of any of Examples 1-42, further comprising a first module and a second module, wherein at least one of the two or more long-distance radiation sources and the one or more short-distance radiation sources is disposed on the first module, and wherein the spectral detector is disposed on the second module.

In Example 44, the spectral sensor of any of Examples 1-43, wherein the processor is configured to activate the visual indicator to visually indicate a direction of rotation of the spectral sensor to achieve more effective determination of the physiologic parameter of the underlying myocardial tissue.

In Example 45, the spectral sensor of any of Examples 1-44, wherein the processor is configured to activate the visual indicator to visually indicate a direction of translation of the spectral sensor to achieve a closer proximity of the at least one radiation source to the tissue of the myocardium.

In Example 46, the spectral sensor of any of Examples 1-45, wherein the visual indicator comprises at least one light visible on the spectral sensor when the spectral sensor is placed against the intercostal space.

In Example 47, the spectral sensor of any of Examples 1-46, further comprising providing a haptic feedback device to further indicate the direction of position adjustment.

In Example 48, a system according to an embodiment of the present invention includes an electrode assembly comprising a sternum electrode coupled to an apex electrode; and a pocket coupled to the sternum and apex electrodes so as to be arranged over an intercostal space over a heart of a patient when the sternum electrode is properly positioned on the right sternum and the apex electrode is properly positioned on the left torso, wherein the pocket is sized to receive a spectral sensor for measuring a physiologic parameter of a myocardium of the heart of the patient.

In Example 49, the system of any of Examples 1-48, wherein the pocket further comprises a window configured for placement against skin of the patient, wherein the window is sized sufficiently to permit radiation to be emitted from the spectral sensor toward the myocardium by one or more radiation sources, and to be received from the myocardium to the spectral sensor by one or more detectors.

In Example 50, a system according to an embodiment of the present invention includes an electrode assembly comprising a sternum electrode coupled to an apex electrode; and a spectral sensor coupled to the sternum and apex electrodes so as to be arranged over an intercostal space over a heart of a patient when the sternum electrode is properly positioned on the right sternum and the apex electrode is properly positioned on the left torso, wherein the spectral sensor is configured to measure a physiologic parameter of a myocardium of the heart of the patient.

In Example 51, a method for measuring a myocardial physiologic parameter according to an embodiment of the present invention includes placing an at least partially convex portion of a spectral sensor against an intercostal space of a human over a heart of the human and measuring the physiologic parameter of a myocardium of the heart with the spectral sensor over time during an emergency medical event.

In Example 52, the method of any of Examples 1-51, further comprising attaching the spectral sensor to the intercostal space with adhesive.

In Example 53, the method of any of Examples 1-52, further comprising pressing the spectral sensor into the intercostal space.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
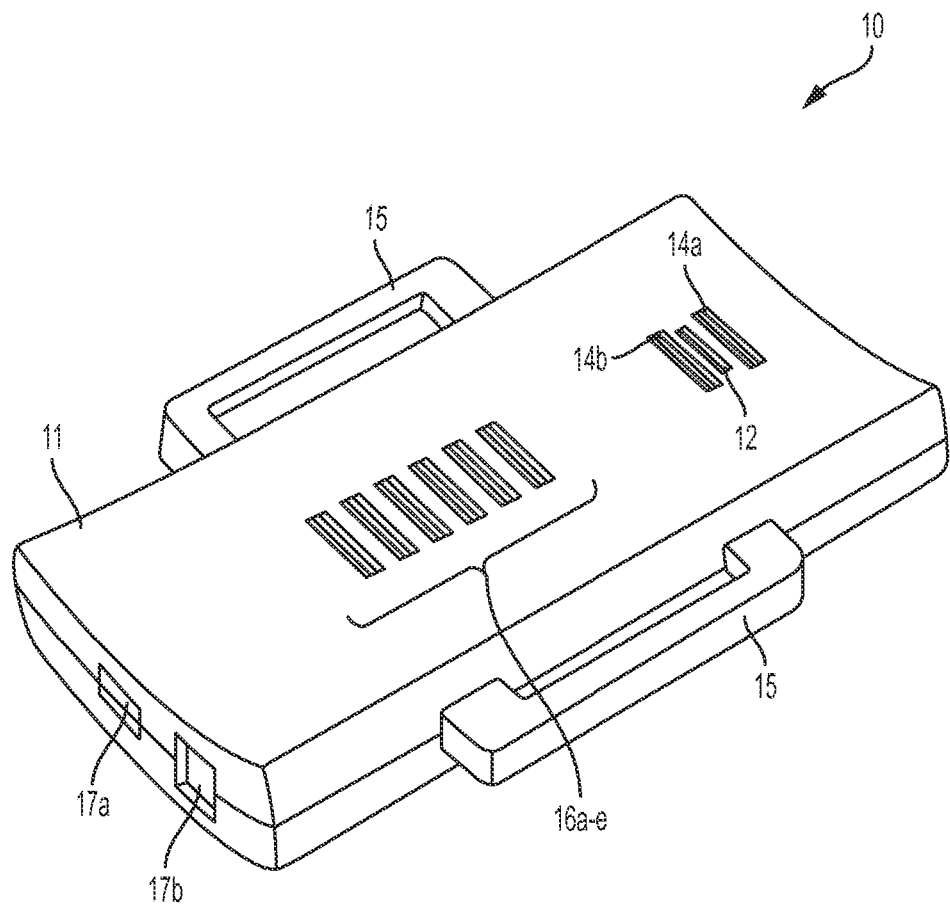
FIG. 1 illustrates a prior art spectral sensor.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 3:
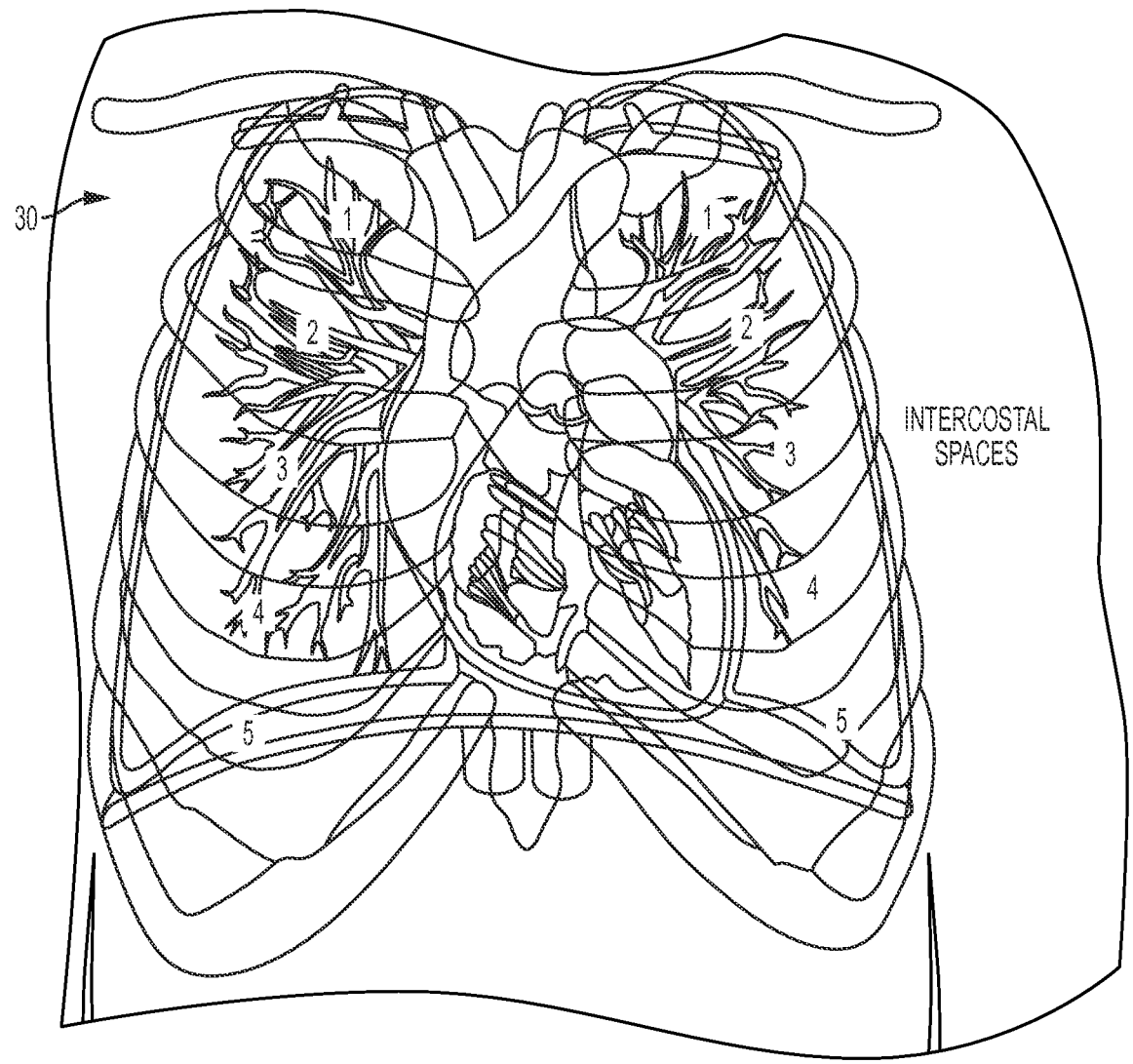
FIG. 3 illustrates a front view of a human thoracic cavity, illustrating intercostal spaces and the human heart.
Figure 4A:
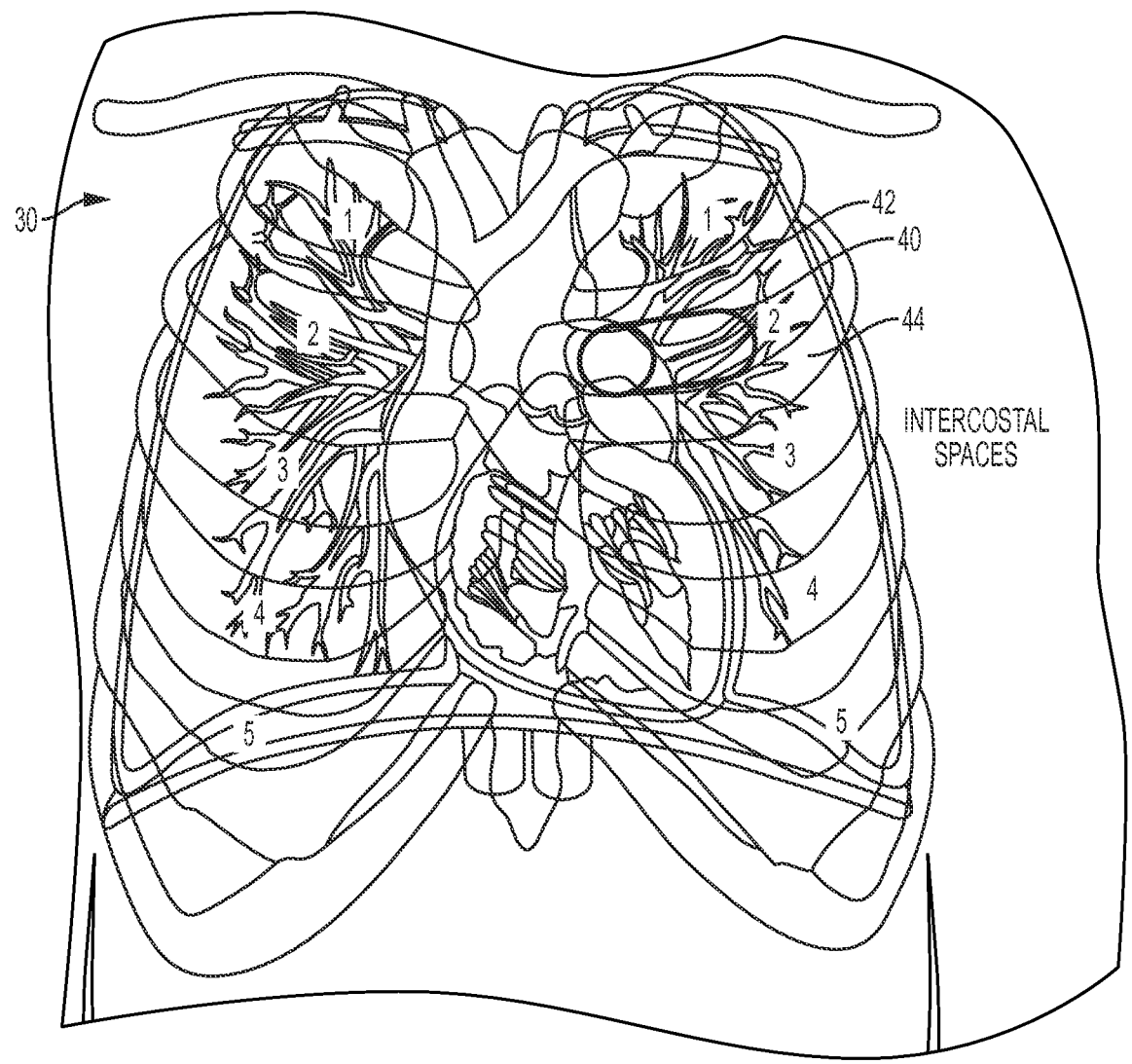
FIG. 4A illustrates placement of an intercostal spectral probe in the front view of FIG. 3, according to embodiments of the present invention.
Figure 5:
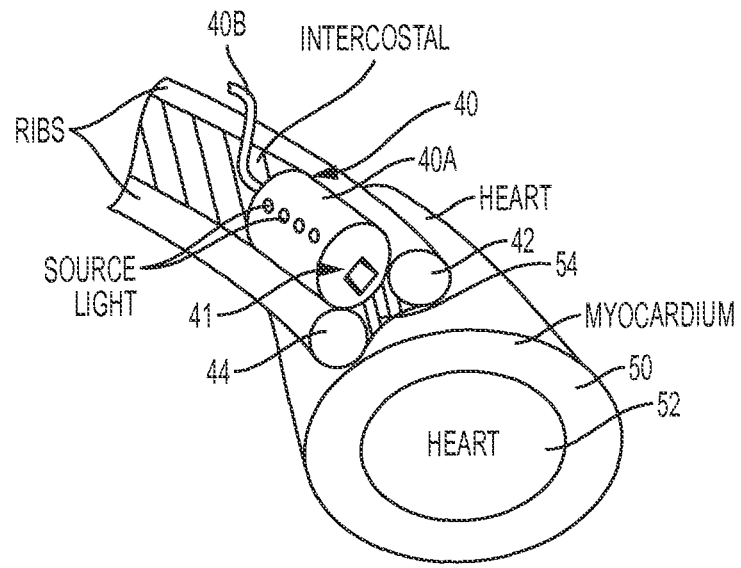
FIG. 5 illustrates a partial cross-sectional perspective view of the placement of the intercostal spectral probe of FIG. 4A, according to embodiments of the present invention.
Figure 6:
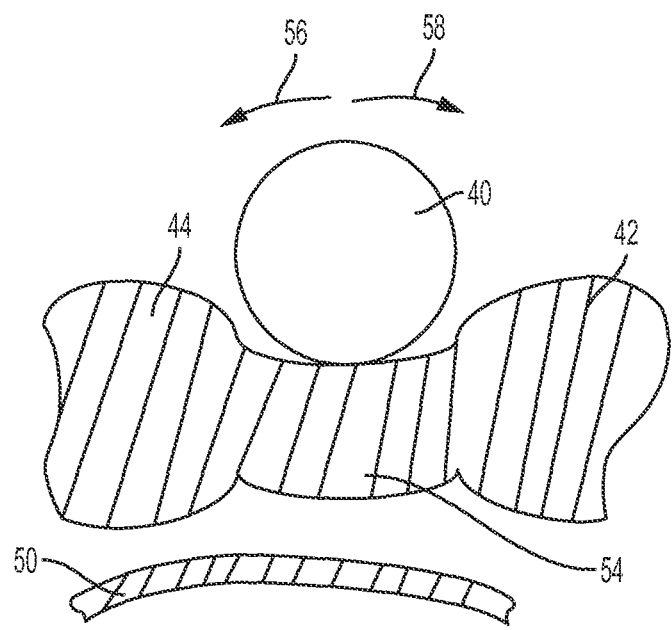
FIG. 6 illustrates a side cross-sectional view of the placement of the intercostal spectral probe of FIGS. 4A and 5, according to embodiments of the present invention.
Figure 8:
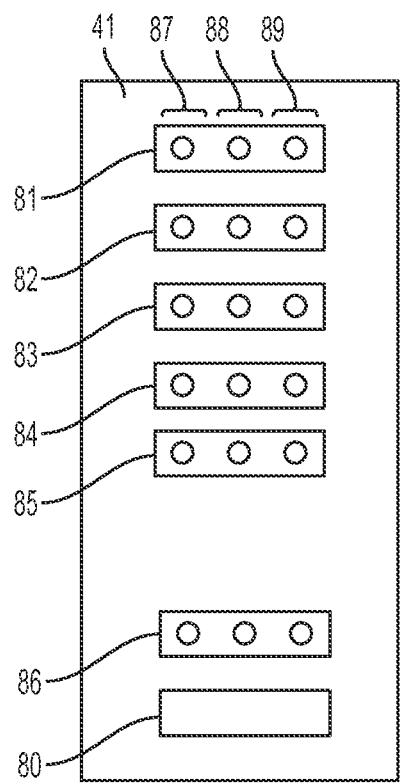
FIG. 8 illustrates a bottom view of an optical spectroscope housed in a sensor probe, according to embodiments of the present invention.

FIG. 3 illustrates a front view of a human thoracic cavity 30, illustrating intercostal spaces and the human heart, including the first (1), second (2), third (3), fourth (4), and fifth (5) left and right intercostal spaces, which are the spaces between the ribs. FIG. 4A illustrates placement of an intercostal spectral sensor, which may also be referred to as an intercostal spectral probe 40, in the second left intercostal space between ribs 42 and 44, according to embodiments of the present invention. According to other embodiments, the intercostal spectral probe/sensor 40 is placed in the third or fourth intercostal space. As shown in FIGS. 5 and 6, the tissue 54 between ribs 42 and 44 and under the intercostal space, including the user's skin, is relatively thick, and the myocardium 50 of the heart 52 is underneath tissue layer 54. Also, in many cases, the myocardium 50 is not directly below one of the intercostal spaces, but is rather offset superior or inferior of the intercostal space. Thus, existing spectral sensors 10 are neither shaped nor configured to measure myocardial physiologic parameters. The probe 40 includes a support structure 40A that provides a housing for the optical spectroscope 41. As shown in FIG. 8, the optical spectroscope 41 includes at least one emitter 81-86 and at least one spectral receiver 80. The spectral receiver 80 may be an integrated, miniaturized spectral bench made up, for example, of a diffraction grating and a complementary metal-oxide-semiconductor (CMOS) image sensor. The spectral receiver 80 may also include an optical waveguide (e.g., constructed using a lens and fiber optics) that directs the incident light back to a longer handle (not shown) of the probe 40 and/or back to a patient monitor (e.g., patient monitor 154 depicted in FIG. 12). The optical spectroscope 41 may transmit the raw spectroscopic data back to the patient monitor 154 for processing and determination of a magnitude of effectiveness of the radiation source (e.g., the at least one emitter 81-86) in illuminating the tissue of the myocardium. The spectroscopic data may also be used to determine physiologic parameters such as, for example, $SmO_2$, pH, hematocrit and $CO_2$. In embodiments, a processor separate from the patient monitor 154 may also be housed in the probe 40 and may be configured to perform one or more of these functions and transmit the results of the functions to the patient monitor 154.

The transmission of data back and forth between the probe 40 and the patient monitor 154 can be accomplished using any number of different types of data communication technologies. For example, communication may be wired (e.g., using a serial and/or parallel cable 40B) and/or wireless and may involve any number of various types of networks. Such networks may be, or include, any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The network may include a combination of multiple networks. Various types of wireless communication may be used and may include, for example, infrared communication, radio frequency (RF) communication (e.g., radiative and/or inductive), acoustic communication, electric communication, and/or the like, and may utilize any number of communication protocols such as, for example, Bluetooth®, IEEE 802.11, and/or the like.

Figure 4B:
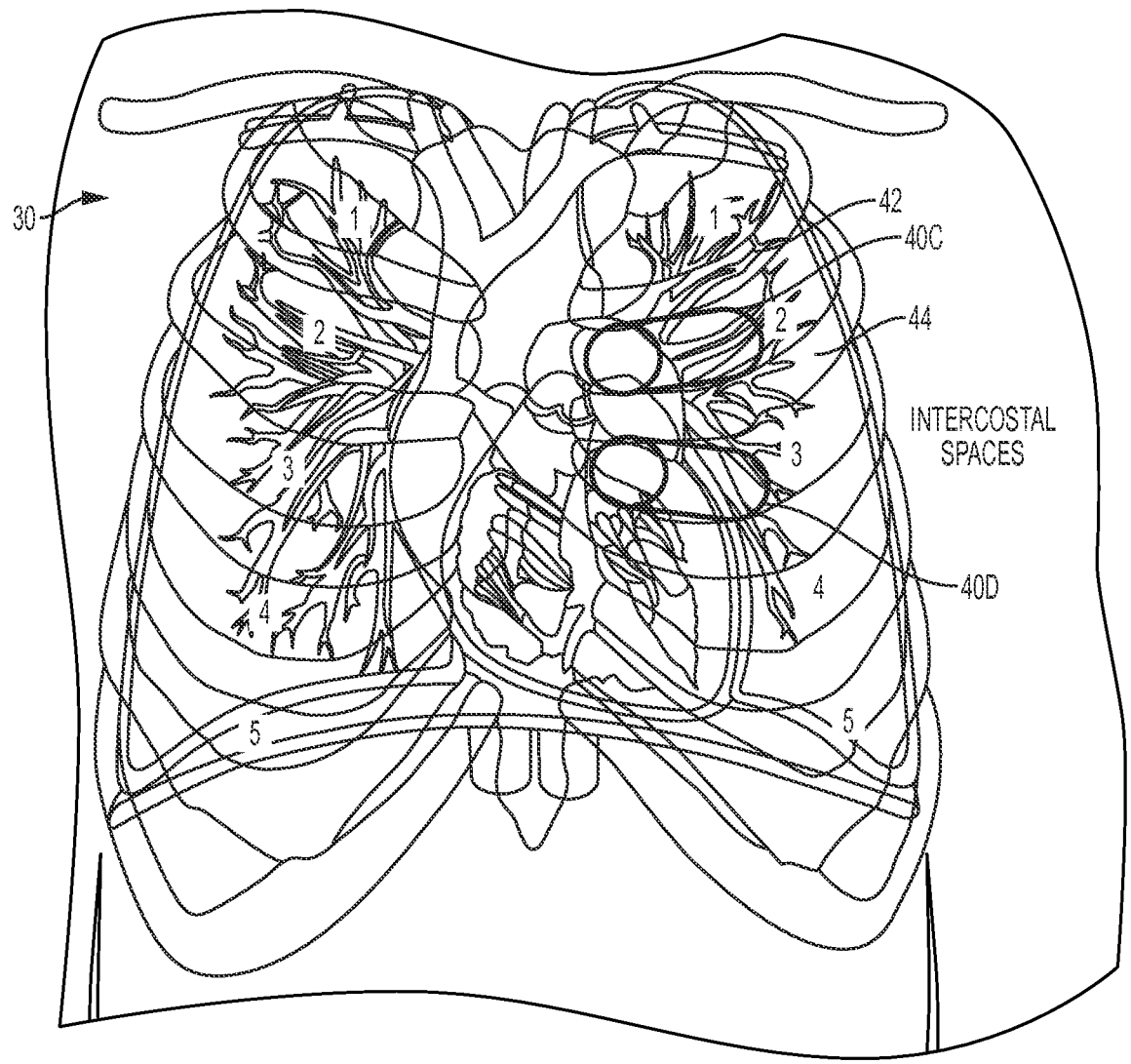
FIG. 4B illustrates placement of two portions of a modular intercostal spectral probe in the front view of FIG. 3, according to embodiments of the present invention.

As shown, for example, in FIG. 4B, embodiments may include a modular intercostal spectral probe that includes two or more independent modules 40C and 40D. In this manner, one or more modules may be positioned in different intercostal spaces, as shown in FIG. 4B. A first module 40C may include the at least one emitter 81-86, and a second module 40D may include the at least one spectral receiver 80 (e.g., spectral bench). In embodiments, the first and second modules 40C and 40D may be configured to communicate with one another via wired and/or wireless communication. In some embodiments, each of the first and second modules 40C and 40D may include visual indicators to aid in positioning, as described in further detail below. In other embodiments, only one of the first and second modules 40C and 40D (or less than all of the modules) may include the visual indicators. That is, for example, it may be more important to achieve a particular position and/or orientation of the second module 40D (containing the receiver) and, accordingly, in some embodiments, only the second module 40D includes visual indicators for positioning. According to various embodiments, the modular probe may include a number of emitter modules 40C and/or a number of receiver modules 40D, and any one or more of the modules may be configured to communicate with the patient monitor 154, as described above.

Noninvasive physiologic parameter measurements of the myocardium 50 according to the embodiments of the present invention provide clinicians, for example clinicians in an emergency medical situation, with valuable information about the lining of the heart itself; this information cannot be obtained with the same level of relevance from peripheral muscle tissues, whose pH tends to drop sooner and faster than that of the myocardium 50. Furthermore, skeletal muscle pH varies considerably within the human body, so skeletal muscle pH readings are not always able to be reliably correlated with myocardial pH. Measuring myocardial pH can be used to track blood flow to the heart. The same is true for other physiologic parameters like oxygen tension and saturation. Current practices for measuring blood flow as well as the physiologic status of the myocardial tissue can be highly invasive and not at all practical in either the pre-hospital setting or in the hospital setting outside of the thoracic surgery suite or catheterization laboratory.

The probe 40 may be cylindrical in shape, and/or may include a cylindrical or otherwise convex outer surface configured to either rest within the intercostal space, as shown in FIGS. 5 and 6. In this manner, the convex outer surface, for example a cylindrical outer surface, which contains a spectral bench (i.e. two or more spectral radiation sources and at least one spectral detector) may be placed closer to the myocardium 50 than would be possible with a skin interface surface of flat or concave shape, according to embodiments of the present invention.

While the probe 40 is shown in FIG. 4 as being placed into the third or fourth left intercostal space because such intercostal space is closest to the ventricular myocardium 50 tissue of interest, another intercostal space may be used. For instance, the second intercostal space may be used to get an estimate associated with atrial tissue.

Figure 7:
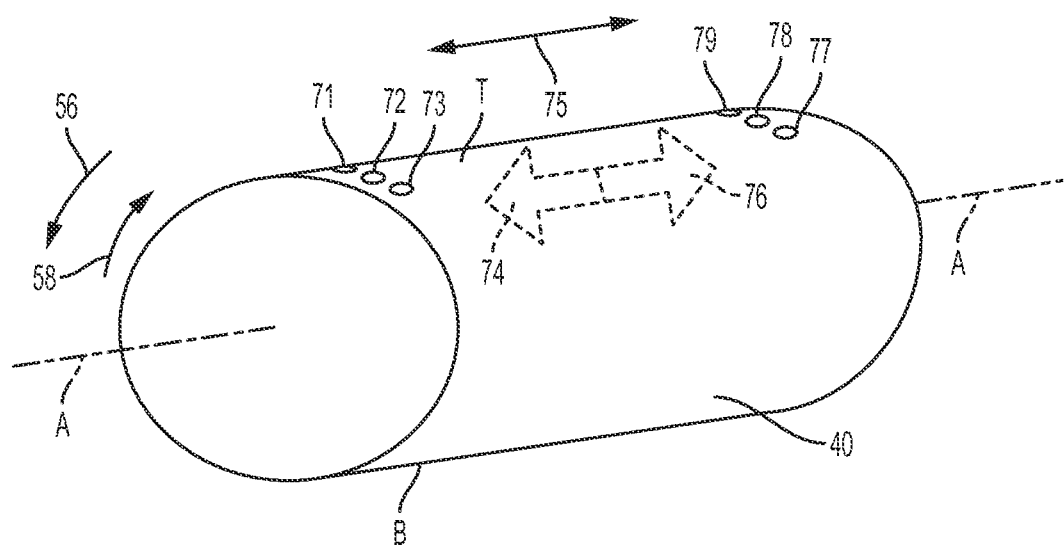
FIG. 7 illustrates a top front perspective view of an intercostal spectral probe, according to embodiments of the present invention.

FIG. 7 illustrates a top front perspective view of an intercostal spectral probe 40, according to embodiments of the present invention. Probe 40 includes visual indicators that assist a user in positioning (which, as used herein, includes orienting) the probe 40 in the intercostal space so as to more or most effectively enable the probe 40 to measure physiologic parameters associated with the myocardium 50. In some embodiments, the probe 40 can evaluate the effectiveness with which it can measure the physiologic parameters based on the effectiveness with which the probe 40 can illuminate the tissue of the underlying myocardium 50.

Figure 2:
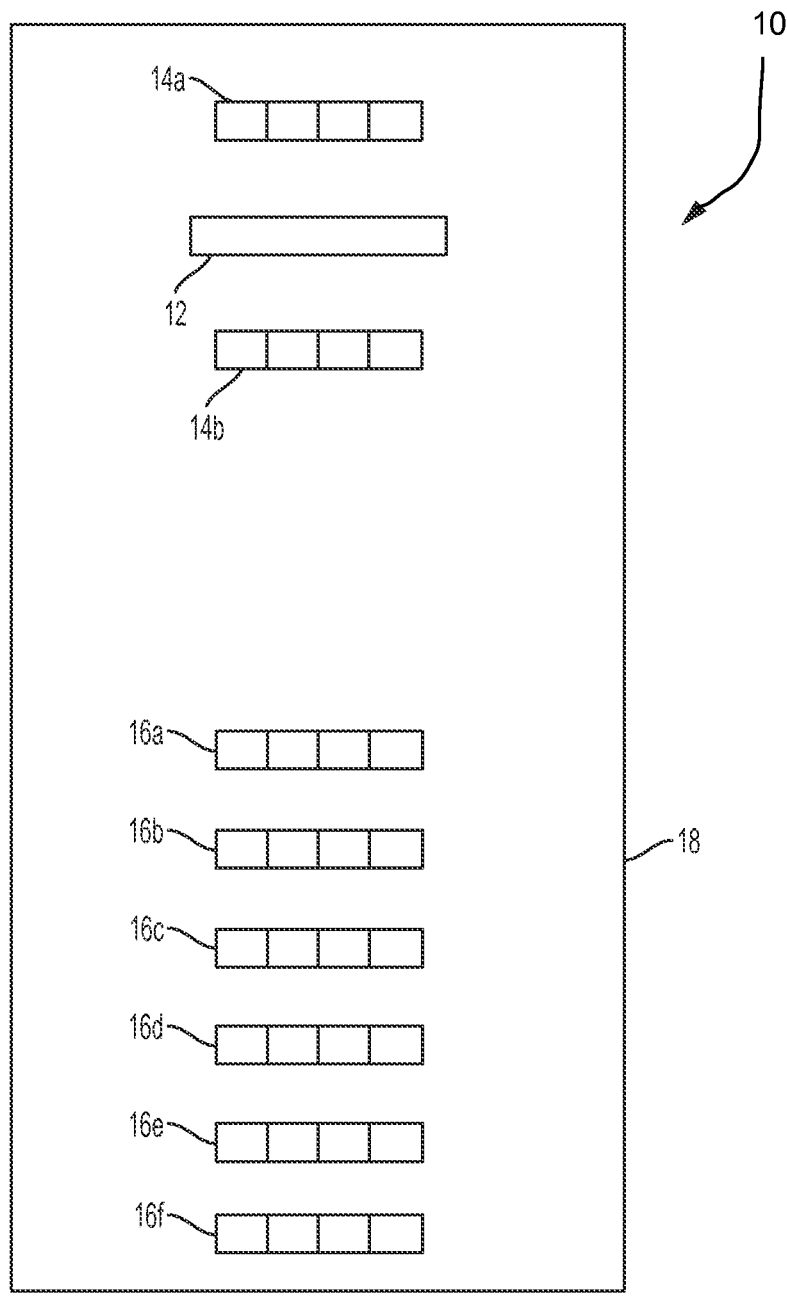
FIG. 2 illustrates a bottom schematic view of placement of radiation sources and a detector of the prior art spectral sensor of FIG. 1.

As shown in FIG. 7, a top T of the probe 40 may include one or more visual indicators 71-73 and 77-79 visible to a user of the probe 40 while the probe 40 is placed in the intercostal space with the top T facing upwardly and/or outwardly and/or along a direction that is not hidden against the body. The bottom B of the probe 40 may include a spectrographic bench (not shown in FIG. 7), similar to that shown in FIG. 2 or 8, according to embodiments of the present invention. Such spectrographic bench may take numerous forms and shapes, and may in some embodiments be convex or at least partially convex so as to be accommodated in the intercostal space. Any of the probes 40 described herein may include any or a subset of the hardware, software, characteristics, and/or performance of any of the spectral sensors and related functionality described in the '535 Publication, according to embodiments of the present invention. The probe 40 may, in some embodiments, be a cylinder or partial cylinder formed about a central axis or axis of rotation A, according to embodiments of the present invention.

As described in the '535 Publication, a processor (such as processor 150 shown in FIG. 12) may be configured to select a suitable long-distance source of the plurality of long-distance sources (such as, for example, the plurality of long-distance sources 81-85 shown in FIG. 8) which most effectively illuminates the tissue of interest (for example, the myocardium 50), according to embodiments of the present invention. In the same way, the processor 150 may be configured to determine a strength or magnitude of the strongest illumination of the tissue of interest, for example the myocardium 50. The processor 150 may be configured to determine such a strength or magnitude of the strongest illumination, and/or identify the particular long-distance radiation source which is responsible for most strongly illuminating the target tissue, at multiple different positions of the probe 40 with respect to the intercostal space. In some embodiments, by determining the strength or magnitude of illumination, the processor 150 can evaluate the effectiveness with which a physiologic parameter associated with the tissue of interest can be determined.

Using these magnitude observations and comparisons, as well as known information about the placement of the long-distance radiation sources 81-85 and/or short-distance radiation sources 86 and/or detector 80, the processor 150 may calculate a spatial orientation adjustment of the probe 40 with respect to the target tissue that would result in increased illumination of the target tissue by one or more of the long-distance radiation sources 81-85 to permit effective determination of the physiologic parameters of the tissue.

For example, if the processor 150 notices that the strongest long-distance illumination magnitude of the myocardial tissue for measuring physiologic parameters is getting weaker as probe 40 is rotated or rolled, for example about central longitudinal axis A of probe 40 along direction 56, the visual indicators 73 and/or 77 may illuminate or change color or be otherwise activated to visually signal that the user should rotate or roll the probe 40 in direction 58 in order to achieve better tissue illumination for measuring physiologic parameters of the myocardium 50, according to embodiments of the present invention. If the processor 150 notices that the strongest long-distance illumination magnitude is getting weaker as probe 40 is rotated or rolled, for example about central longitudinal axis A of probe 40 along direction 58, the visual indicators 71 or 79 may illuminate or change color or be otherwise activated to visually signal that the user should rotate or roll the probe 40 in direction 56 in order to achieve better tissue illumination for measuring physiologic parameters of the myocardium 50, according to embodiments of the present invention. According to such embodiments, the central visual indicator 72 and/or 78 may illuminate to indicate to the user that the rotational position of the probe 40 is sufficient for accurate or effective measurement of the myocardial physiologic parameters.

In some embodiments, processor 150 can also be directly or indirectly coupled with an electrocardiogram (ECG) sensor configured to monitor electrical activity related to a patient's heart, and to generate an ECG trace. Processor 150 can monitor the generated ECG trace while simultaneously monitoring time-varying spectroscopic data from optical spectroscope 41, and can calculate a cross-correlation between these two signals. Since in some examples, observable parameters of the patient's myocardium is expected to be closely correlated with the patient's ECG trace, the time-varying spectroscopic data received by optical spectroscope 41 can also be expected to closely correlate with the patient's ECG trace when optical spectroscope 41 is properly illuminating and imaging the patient's myocardium. Therefore, processor 150 can calculate a cross-correlation coefficient between (i) the patient's ECG trace (or a parameter derived from the patient's ECG trace) and (ii) spectroscopic data from optical spectroscope 41, and use the cross-correlation coefficient as a measure of how effectively the radiation source (e.g., the at least one emitter 81-86) is illuminating the tissue of the myocardium, and/or how effectively the optical spectroscope 41 can determine a physiologic parameter of the patient's myocardium. The cross-correlation coefficient can be calculated using statistical comparisons as known to a person of skill. The cross-correlation coefficient can therefore provide a mathematical indication of the correlation between the ECG data and the spectroscopic data. If processor 150 detects that the cross-correlation is decreasing as probe 40 is translated or rotated in one direction, the visual indicators can visually signal the user to move probe 40 in the opposite direction. If processor 150 detects that the cross-correlation is increasing as probe 40 is translated or rotated in one direction, the visual indicators can visually signal the user to continue moving probe 40 in that direction.

According to some embodiments of the present invention, the visual indicators 71-73 and 77-79 are lateral position indicators. In some embodiments, one set of lateral position indicators 71-73 are located on the top T of the probe 40, and are used to inform the user whether to translate the entire probe 40 (e.g. without rotation about axis A). For example, if probe 40 should be moved along either direction perpendicular to arrow 75, one of visual indicators 71, 73 may be activated to indicate the direction of lateral translation that has been determined to improve an illumination of the desired tissue by the long-distance radiation source or sources. The middle visual indicator 72 may be configured for activation when the processor 150 determined that the lateral position (e.g. translation) is as desired, or within a certain range thereof.

According to some embodiments, the probe 40 includes two lateral position indicators, one being set 71-73, the other being set 77-79. These lateral position indicators function similarly to those described above, except they are configured to indicate rotation about an vertical axis that is perpendicular to axis A. In other words, each set indicates lateral position information with respect to each particular end of sensor with which it is associated. If visual indicators 71 and 77 are activated, a clockwise rotation (viewed from above) is indicated; if visual indicators 73 and 79 are activated, a counterclockwise rotation (viewed from above) is indicated. If visual indicator 72 is activated along with visual indicator 77, this may indicate that the user is to leave the end of probe 40 at which indicator 72 is located stationary, while moving the end at which visual indicator 77 is located in the lateral direction indicated, according to embodiments of the present invention.

An inertial sensor system, such as the Analog Devices ADIS164362 Tri-Axis Gyroscope Accelerometer, may be used. These inertial sensors may be used to map both the rotational position of the probe 40, as well as its longitudinal position along the intercostal space.

Probe 40 may further include longitudinal translation indicators 74, 76, which visually indicate repositioning of the probe 40 along the directions indicated by arrow 75, according to embodiments of the present invention. For example, arrow 74 may be illuminated or its color changed or otherwise activated to indicate translation of the entire probe 40 along direction 75, for example, along axis A, while arrow 76 may be illuminated or its color changed or otherwise activated to indicate translation of the entire probe 40 along the opposite direction indicated by arrow 75.

Visual indicators 71-74 and 76-79 may take various forms, shapes, and arrangements, and one of ordinary skill in the art, based on the present disclosure, will appreciate that numerous other visual indicators may be used to achieve the described functionality. The visual indicators may be lights, including for example light emitting diodes (LEDs). Different colors, and/or flashing patterns, and/or brightnesses may be employed. Further, audio and/or haptic feedback devices may be included, either in addition to or instead of visual indicators, to provide positioning and/or placement feedback. Additional visual or other indicators may also be used to alert the user that the probe 40 is correctly placed and measuring myocardial physiologic parameters, so that the user may then secure the probe 40 in its current orientation and placement, for example with adhesive and/or a strap. This strap may be a strap that wraps around the chest of the patient and applies a slight or strong downward force of the probe 40 into the intercostal space, to improve illumination of the myocardial tissue, according to embodiments of the present invention. In this manner, the strap or other device that may be used to maintain the position of the probe 40 may also prevent environmental light (or at least a portion thereof) from interfering with the operation of the probe 40.

The long-distance radiation sources 81-85 shown in FIG. 8 may each include LEDs (separate LEDs are shown in columns 87, 88, and 89 for each radiation source 81-85). In some cases, the LEDs of each source 81-85 produce a relatively broad bandwidth incident radiation for illuminating the myocardium tissue. In other cases, each LED of each column 87, 88, 89 emits radiation at a different wavelength and/or wavelength profile, and the positional adjustment features described above may be used to position the probe 40 such that the most preferred wavelength best illuminates the target tissue, according to embodiments of the present invention.

Because the intercostal tissue 54 is thicker (and thus provides more scattering of applied light radiation) and the myocardium 50 deeper than the tissues that would normally be illuminated for physiologic parameter measurement by sensors such as sensor 10, in some embodiments the LEDs of one or more of the radiation sources 81-85 may be replaced with higher intensity light sources, for example lasers of tunable wavelength, which permit greater depth penetration of illuminating radiation, according to embodiments of the present invention. According to some embodiments of the present invention, the radiation from radiation sources 81-85 may be used by the detector 80 and processor 150 to differentiate between muscle and bone.

Figure 9:
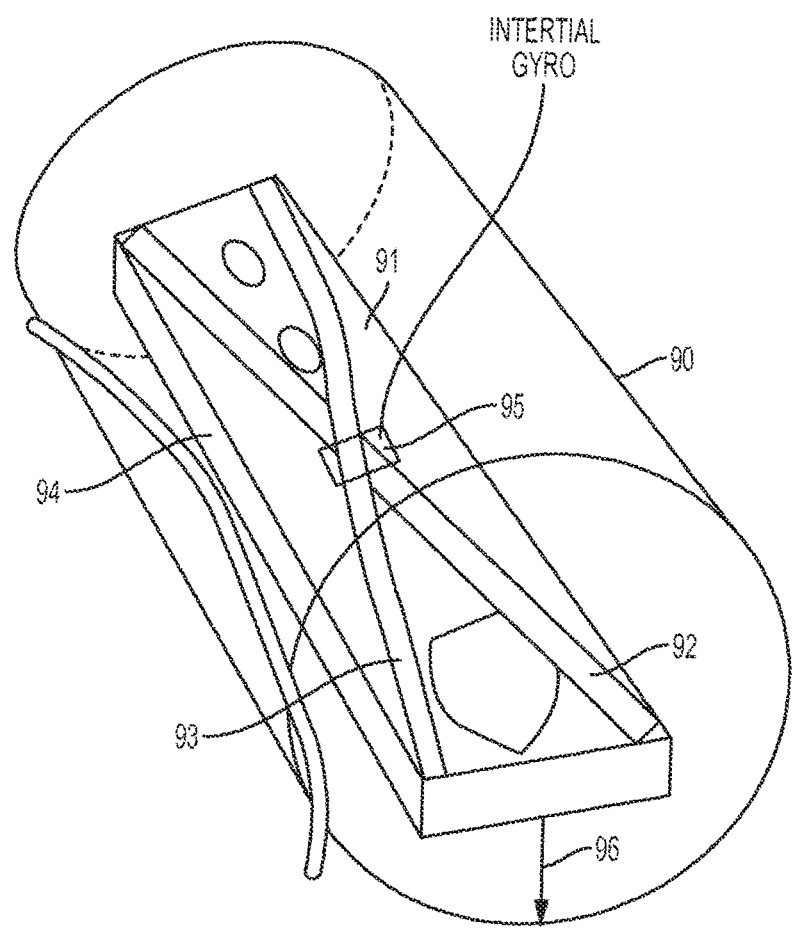
FIG. 9 illustrates a translucent view of an intercostal spectral probe, according to embodiments of the present invention.

FIG. 9 illustrates a translucent view of an intercostal spectral probe 90, according to embodiments of the present invention. Probe 90 is flexible, and includes a circuit board or platform 91 including a spectrographic bench (examples of which are described above) configured to face toward the patient (e.g. along arrow 96). The platform 91 may be reinforced by one or more rods 92 which are relatively rigid to prevent torsional distortion of the spectrographic bench upon deformation of the probe 90. For example, the platform 91 may be rotatable about a longitudinal axis, and the probe 90 may be bent or flexed in the manner shown by line 94, and an internal gyroscope 95 may be configured to permit the spectrographic bench to face downwardly along arrow 96 throughout such bending or deformation, according to embodiments of the present invention. According to some embodiments, the body of the probe 90 is made of a polymer material that may be semi-conformable and/or semi-rigid, for example with a durometer of 20 on the A Scale.

Figure 10:
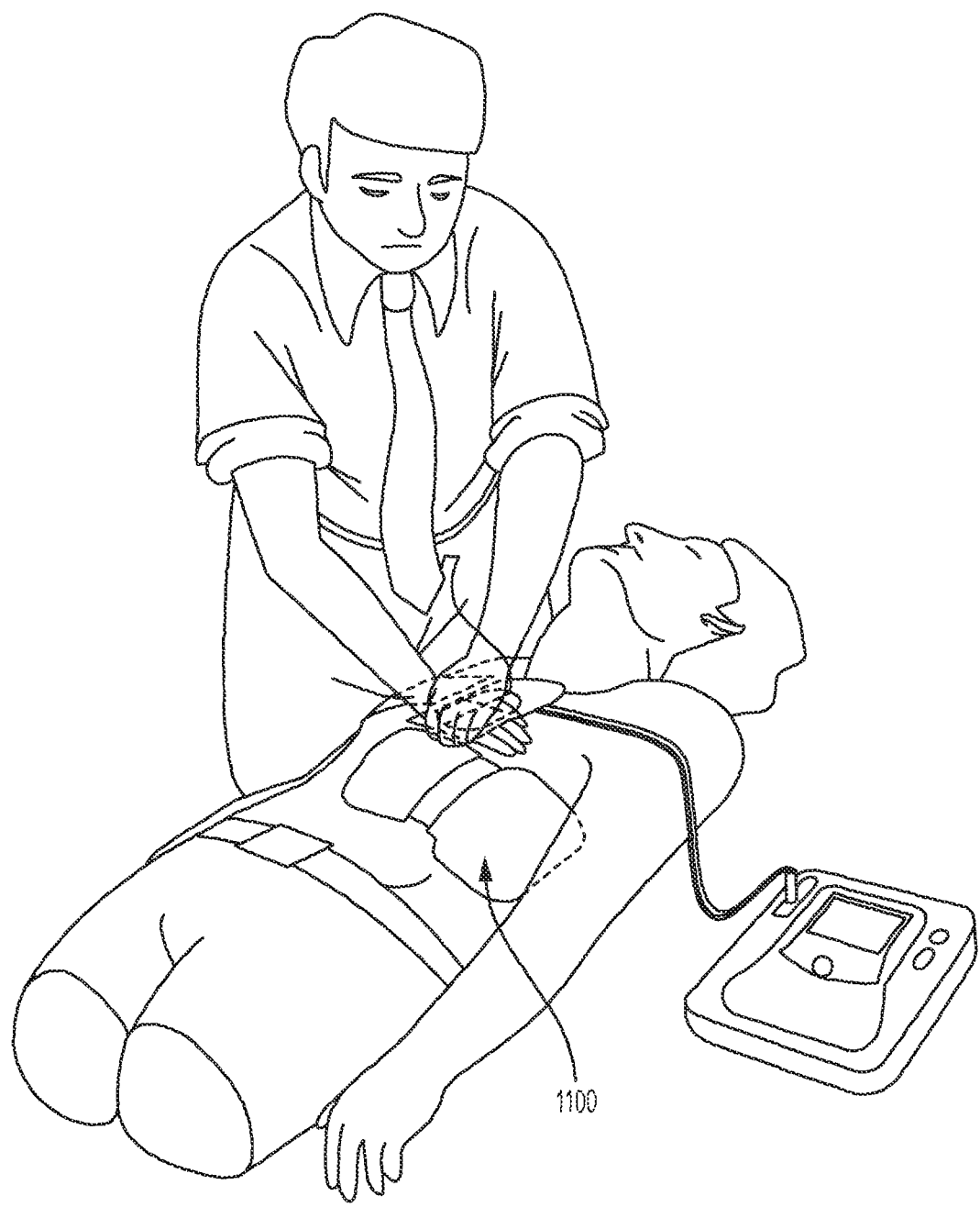
FIG. 10 illustrates a front perspective view of a human chest illustrating typical placement of external electrodes for defibrillator-based cardiac monitoring and defibrillation.
Figure 11:
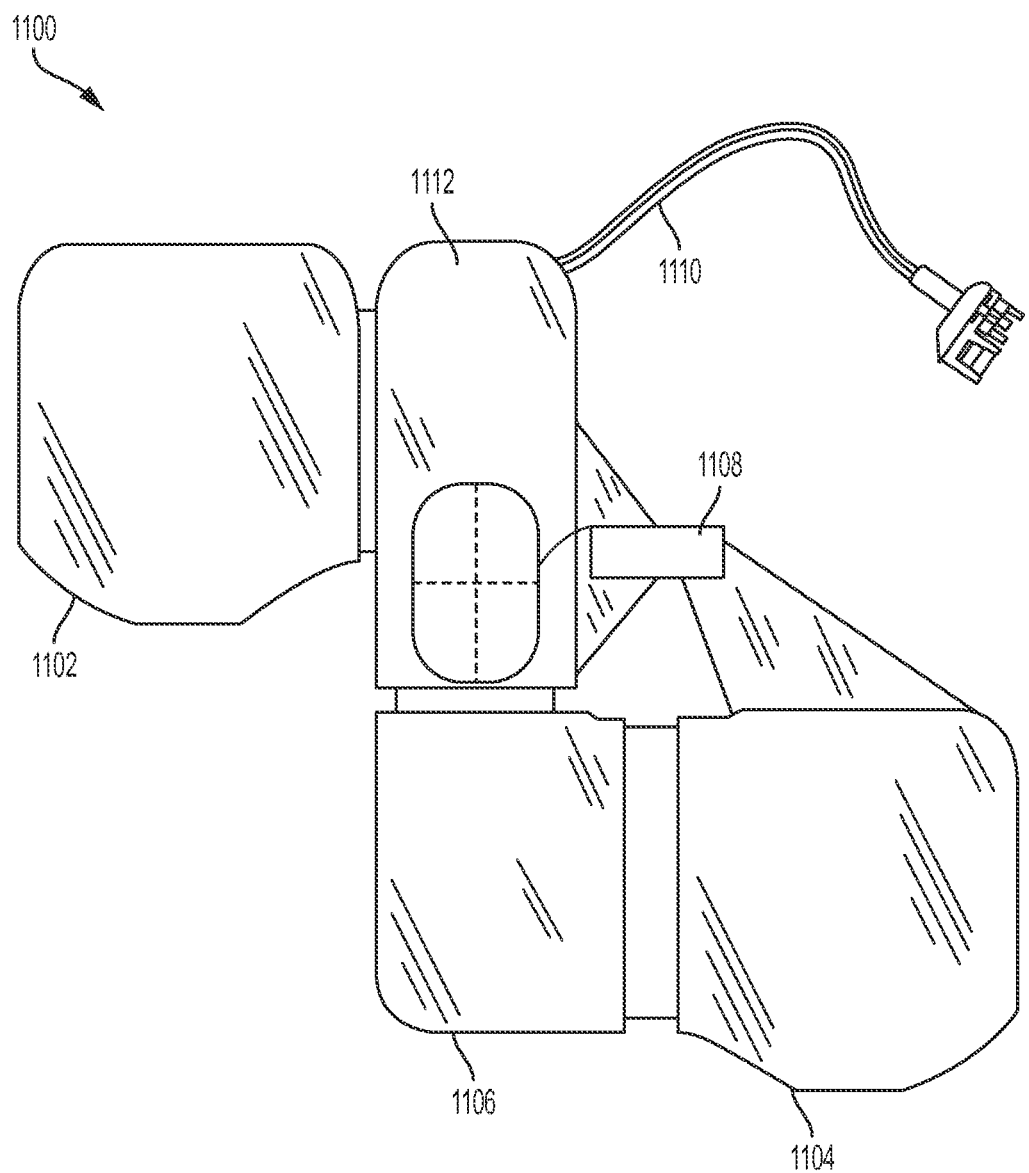
FIG. 11 illustrates a front view of the electrode assembly of FIG. 10 with an added intercostal spectral probe or probe accommodation pocket, according to embodiments of the present invention.

FIG. 10 illustrates a front perspective view of a human chest illustrating typical placement of external electrodes for defibrillator-based cardiac monitoring and defibrillation, while FIG. 11 illustrates a front view of the electrode assembly of FIG. 10 with an added intercostal spectral sensor 1108 or sensor accommodation pocket 1108, according to embodiments of the present invention. According to some embodiments, the electrode system 1100 of FIGS. 10 and 11 is similar to that shown and described in U.S. Patent Application Publication No. 2014/0135666, published on May 15, 2014 ("the '666 Publication"), which is incorporated herein by reference in its entirety for all purposes.

For example, the electrode system 1100 includes a sternum electrode 1102, an apex electrode 1104, a sternal bridge 1106, and a chest compression monitor 1112, according to embodiments of the present invention. A communications cable 1110 communicably couples the electrodes 1102, 1104, and the chest compression monitor 1112 with an additional processor or information system, according to embodiments of the present invention. Also connected, for example mechanically, physically, and/or communicably with some or all of the other components of the system 1100, is a sensor 1108. Sensor 1108 may be a spectral probe 40 as described above, for example. According to other embodiments, element 1108 is a pocket for receiving a probe 40. The positioning of sensor 1108 or pocket 1108 with respect to the system 1100 is such that the probe 40 is placed directly over or into the relevant intercostal space of the patient when the other elements of system 1100 are also properly positioned, according to embodiments of the present invention. If element 1108 is a pocket, then the pocket 1108 may include a window or transparent material or cutout that permits optical interface of the spectrographic bench of a probe 40 with the underlying intercostal space of the patient.

In embodiments, the probe 40 and/or pocket 1108 may be configured to be adjustable. That is, for example, the position of the probe 40 with respect to the system 1100 may be able to be changed by a practitioner. In embodiments, the probe 40 may be removably coupled to the system 1100, slideably coupled to the system 1100, and/or the like. The pocket 1108 may be adjustable such as by being removably coupled to the system 1100, slideably coupled to the system 1100, and/or the like. For example, in an embodiment, the pocket 1108 may include a first portion of a hook-and-loop fastening material (e.g., Velcro®) and the second portion or portions of the hook-and-loop fastening material, which is configured to mate with the first portion, may be disposed at various locations on the system 1108 to allow for adjustment of the position of the pocket 1108. In other embodiments, the pocket 1108 may be attached to the system 1108 using a loop or other engaging structure configured to slideably engage a system of tracks upon which the pocket 1108 can slide. Any number of other mechanisms and techniques may be used to provide an adjustable attachment of the probe 40 and/or the pocket 1108 to the system 1100.

Figure 12:
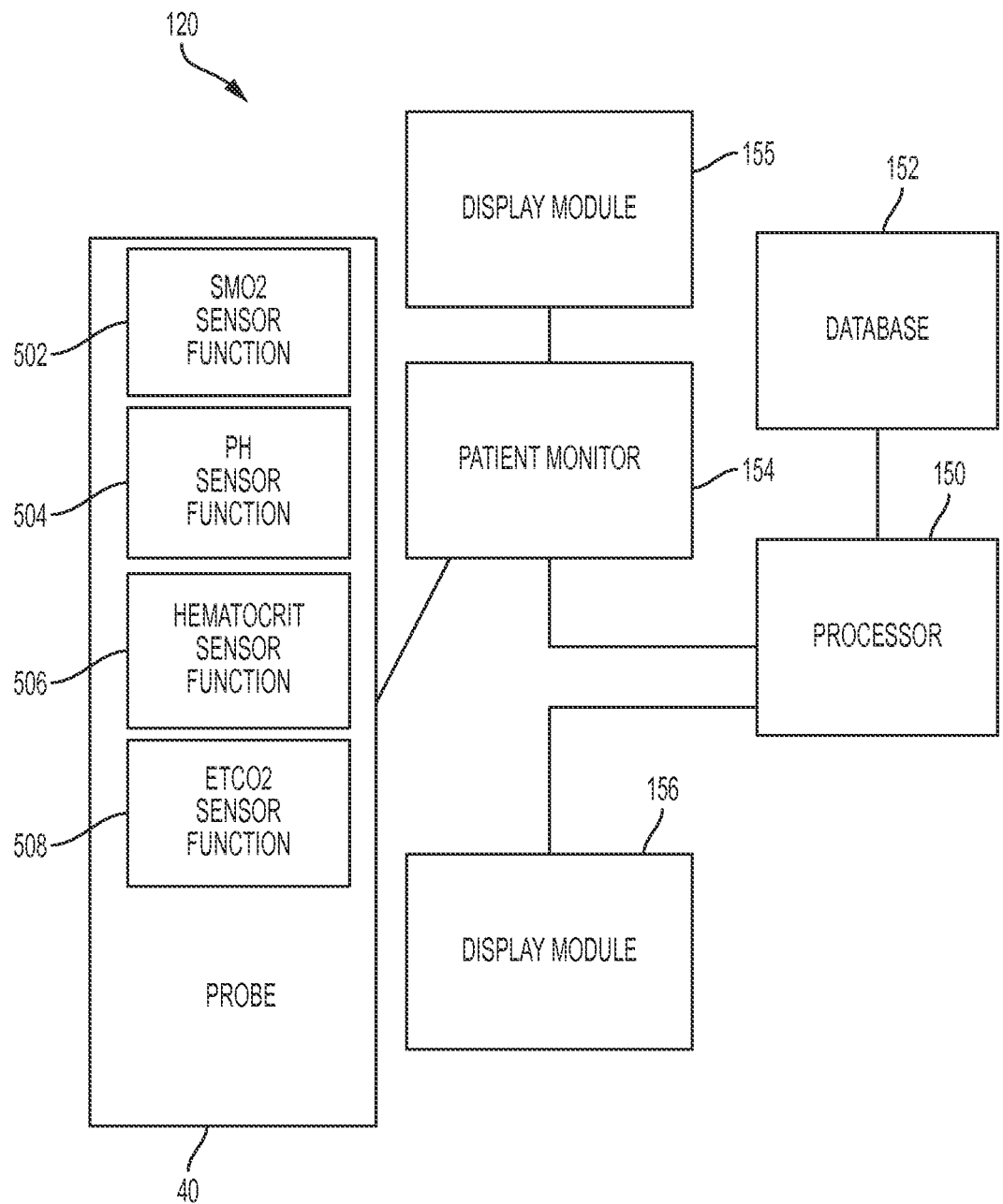
FIG. 12 illustrates a patient monitoring and control system including a spectral sensor, according to embodiments of the present invention.

FIG. 12 illustrates a patient monitoring and control system 120 including a spectral probe 40, according to embodiments of the present invention. A spectral probe 40, which houses an optical spectroscope 41 that is capable of emitting light in a specified wavelength range. The spectra generated from the light scattered and reflected by the underlying myocardial tissue and then detected by the optical spectroscope's 41 detector are then used to implement the functions of e.g., a muscle oxygen saturation sensor 502, a pH sensor 504, a blood hematocrit sensor 506, and/or a carbon dioxide sensor 508, according to embodiments of the present invention, though many other physiologic parameter measurement functions can also be implemented using optical spectroscopic information. Spectral probe 40 is communicably coupled with a patient monitor 154, which may be, for example, a defibrillator or an automatic external defibrillator, according to embodiments of the present invention. Patient monitor 154 may include or otherwise by in communication with a processor 150, which is configured to or otherwise capable of executing all or parts of the methods described herein and/or described in the '535 Publication. A database 152 may be used to store information and/or instructions or other software. The patient monitor 154 may have its own display module 155 in communication therewith, and/or the system 120 may include a separate display module 156, according to embodiments of the present invention.

Information about the myocardial physiologic parameter as measured, or measured over time, by probe 40 may be displayed on the display module 155 of the patient monitor 154 and/or the other display module 156, for example along with other data about a patient to which the probe 40 is applied, according to embodiments of the present invention. Such data or information may also be stored in database 152, for example independently or with other information about the patient or the medical encounter for which the spectral probe's 40 data is being collected.

The illustrative system 120 shown in FIG. 12 is not intended to suggest any limitation as to the scope of use or functionality of embodiments of the present invention. Neither should it be interpreted as having any dependency or requirement related to any single component or combination of components illustrated therein. Additionally, any one or more of the components depicted in FIG. 12 may be, in embodiments, integrated with various ones of the other components depicted therein (and/or components not illustrated), all of which are considered to be within the ambit of the present invention. The hardware elements and/or modules shown in FIG. 12 may be included on the same device and/or distributed across multiple devices, and each such hardware element or module shown in FIG. 12 may have its elements or functionality spread across multiple devices.

Figure 13:
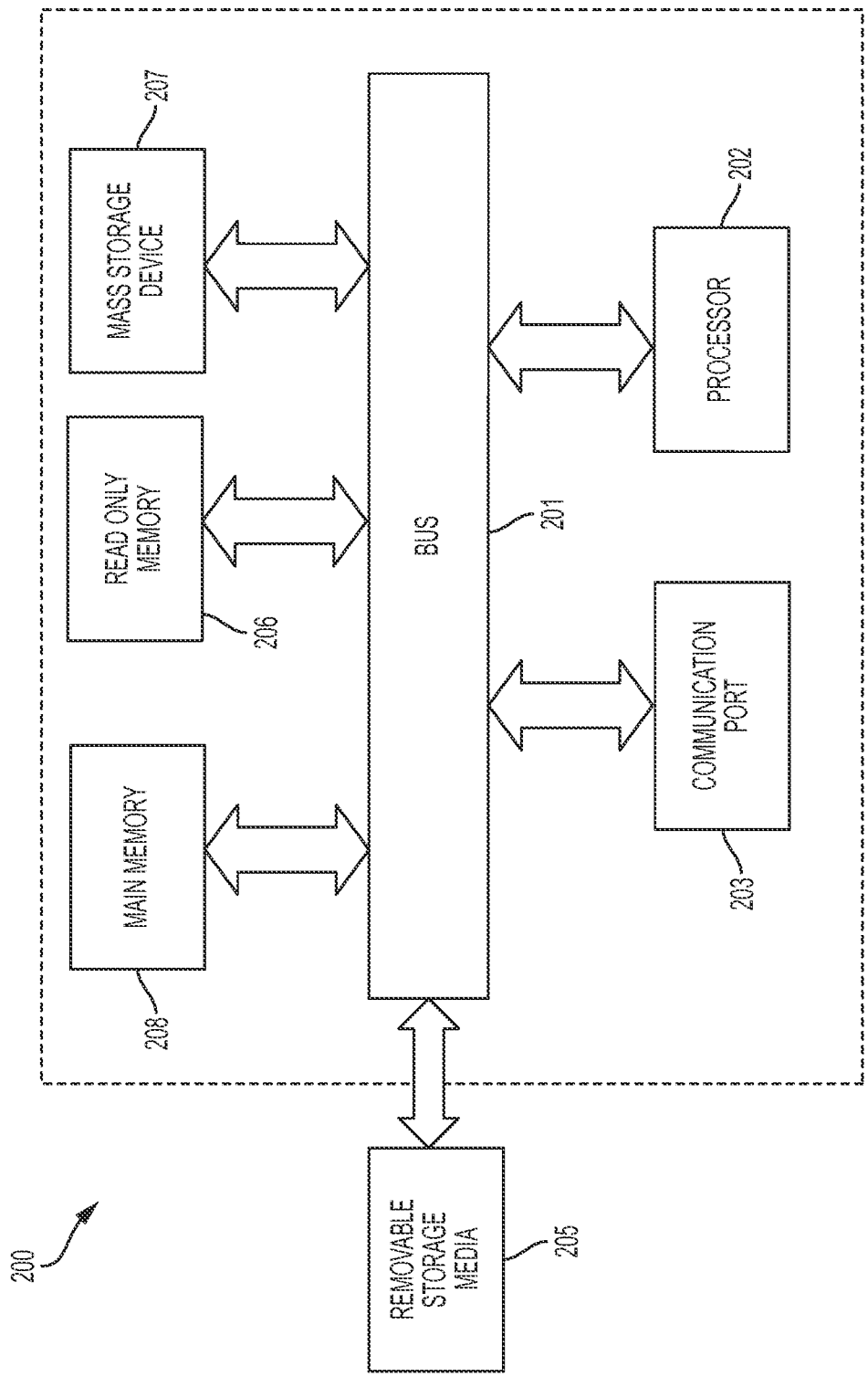
FIG. 13 illustrates a computer system, according to embodiments of the present invention.

FIG. 13 is an example of a computer or computing device system 200 with which embodiments of the present invention may be utilized. For example, defibrillator 154 and/or the display/control system of probe 40 may be or incorporate a computer system 200, according to embodiments of the present invention. According to the present example, the computer system includes a bus 201, at least one processor 202, at least one communication port 203, a main memory 208, a removable storage media 205, a read only memory 206, and a mass storage 207.

Processor(s) 202 can be any known processor, or any known microprocessor or processor for a mobile device. Communication port(s) 203 can be any of an RS-232 port for use with a modem based dialup connection, a copper or fiber 10/100/1000 Ethernet port, or a Bluetooth® or WiFi interface, for example. Communication port(s) 203 may be chosen depending on a network such a Local Area Network (LAN), Wide Area Network (WAN), or any network to which the computer system 200 connects. Main memory 208 can be Random Access Memory (RAM), or any other dynamic storage device(s) commonly known to one of ordinary skill in the art. Read only memory 206 can be any static storage device(s) such as Programmable Read Only Memory (PROM) chips for storing static information such as instructions for processor 202, for example.

Mass storage 207 can be used to store information and instructions. For example, flash memory or other storage media may be used, including removable or dedicated memory in a mobile or portable device, according to embodiments of the present invention. As another example, hard disks such as SCSI drives, an optical disc, an array of disks such as RAID, or any other mass storage devices may be used. Bus 201 communicably couples processor(s) 202 with the other memory, storage and communication blocks. Bus 201 can be a PCI/PCI-X or SCSI based system bus depending on the storage devices used, for example. Removable storage media 205 can be any kind of external hard-drives, floppy drives, flash drives, zip drives, compact disc-read only memory (CD-ROM), compact disc-re-writable (CD-RW), or digital video disk-read only memory (DVD-ROM), for example. The components described above are meant to exemplify some types of possibilities. In no way should the aforementioned examples limit the scope of the invention, as they are only exemplary embodiments of computer system 200 and related components.

Figure 14:
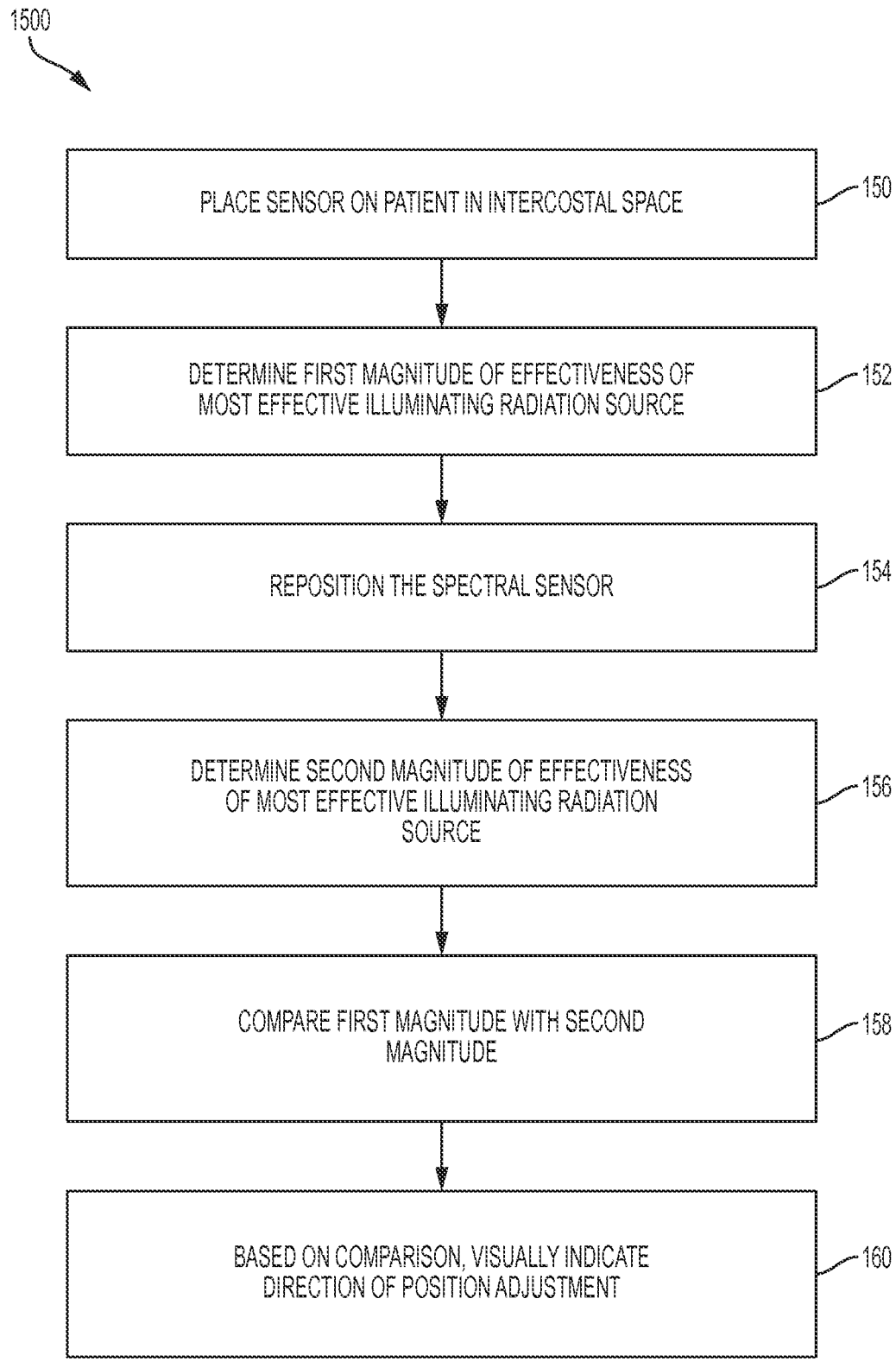
FIG. 14 depicts a flow chart illustrating a method for measuring myocardial pH or other physiologic parameter with an intercostal spectral probe, according to embodiments of the present invention.

FIG. 14 depicts a flow chart 1500 illustrating a method for measuring a myocardial physiologic parameter with an intercostal spectral sensor, according to embodiments of the present invention. A method for measuring a myocardial physiologic parameter includes placing a spectral probe 40 on a patient's skin in a first position in an intercostal space above the patient's myocardium 50 (block 150), wherein the spectral probe 40 comprises two or more long-distance radiation sources 81-85, one or more short-distance radiation sources 86, and a spectral detector 80, at least two of the two or more long-distance radiation sources 81-85 and at least one of the one or more short-distance radiation sources 86 located on the spectral probe 40 at different distances from the spectral detector 80, wherein at least a portion of the spectral probe 40 has a convex outer profile for placement against a concave profile of the intercostal space, as illustrated in FIGS. 4-6. The method may further include selecting a radiation source of the two or more long-distance radiation sources which most effectively illuminates tissue of the myocardium for determining a physiologic parameter of the tissue of the myocardium 50 when the spectral probe 40 is in the first position, and determining a first magnitude of effectiveness of the radiation source in illuminating the tissue of the myocardium 50 in the first position (block 152).

The method may further include repositioning the spectral probe 40 (block 154), for example by rotating or rolling the spectral probe 40 from the first position to a second position in the intercostal space, and determining a second magnitude of effectiveness of the radiation source in illuminating the tissue of the myocardium 50 for determining a physiologic parameter of the tissue of the myocardium 50 when the spectral probe 40 is in the second position (block 156). The first magnitude may be compared with the second magnitude (block 158), and, based on the comparison, the probe 40 may be configured to visually indicate a direction of position adjustment of the spectral probe 40 to achieve more effective illumination of the tissue of the myocardium 50 for determining a physiologic parameter of the tissue of the myocardium 50 by the two or more long-distance radiation sources 81-85 (block 160).

In some embodiments, the convex outer profile of the probe 40 is at least a portion of a cylinder, and wherein rotating or rolling the spectral probe 40 includes rotating the spectral probe 40 about a longitudinal axis A of the cylinder while the spectral probe 40 remains in the intercostal space. Visually indicating the direction of position adjustment may include visually indicating a direction of rotation of the spectral probe 40 to achieve more direct orientation of the two or more long-distance radiation sources 81-85 toward the tissue of the myocardium 50. Visually indicating the direction of position adjustment may include visually indicating a direction of translation of the spectral probe 40 to achieve a closer proximity of the two or more long-distance radiation sources 81-85 to the tissue of the myocardium 50. In some cases, visually indicating the direction of position adjustment comprises illuminating at least one light 71-74, 76-79 visible on the spectral probe 40 when the spectral probe 40 is placed against the skin in the intercostal space.

A spectral probe 40 for measuring a myocardial physiologic parameter according to some embodiments of the invention includes two or more long-distance radiation sources 81-85, one or more short-distance radiation sources 86, a spectral detector 80, wherein at least two of the two or more long-distance radiation sources 81-85 and at least one of the one or more short-distance radiation sources 86 are located on the spectral probe 40 at different distances from the spectral detector 80, and wherein at least a portion of the spectral probe 40 has a convex outer profile for placement against a concave profile of an intercostal space (as illustrated, for example, in FIGS. 4-6). Such a probe 40 may include one or more visual indicators, for example 71-74 and 76-79, as well as a processor (e.g. 150 and/or 202) communicably coupled to the two or more long-distance radiation sources 81-85, the one or more short-distance radiation sources 86, and the visual indicator 71-74 and 76-79, wherein, when the convex outer profile is placed against the concave profile of the intercostal space, the processor 150, 202 is configured to evaluate an effectiveness with which the two or more long-distance radiation sources 81-85 illuminate underlying myocardial tissue, for purposes of determining a physiologic parameter of the underlying myocardial tissue, at various positions of the spectral probe 40 with respect to the intercostal space, and wherein the processor 150, 202 is further configured to, based on the evaluation of the effectiveness, activate the visual indicator (e.g. one or more of 71-74 and 76-79) so as to indicate a direction of position adjustment of the spectral probe 40 to achieve more effective illumination of the tissue of the myocardium 50, for purposes of determining the physiologic parameter of the underlying myocardial tissue.

Such a spectral probe 40 may include a convex outer profile that is at least a portion of a cylinder. The processor 150 may be configured to activate the visual indicator (e.g. one or more of 71-74 and 76-79) to visually indicate a direction of rotation 56, 58, and/or a direction of translation 75, of the spectral probe 40 to achieve more effective illumination of the tissue of the myocardium 50 or a closer proximity of the two or more long-distance radiation sources 81-85 to the tissue of the myocardium 50.

A system according to some embodiments of the present invention includes an electrode assembly 1100 including a sternum electrode 1102 coupled to an apex electrode 1104, and a pocket 1108 coupled to the sternum 1102 and apex 1104 electrodes so as to be arranged over an intercostal space over a heart 52 of a patient when the sternum electrode 1102 is properly positioned on the right sternum and the apex electrode 1104 is properly positioned on the left torso (e.g. as shown in FIG. 10), wherein the pocket 1108 is sized to receive a spectral probe 40 for measuring a physiologic parameter of a myocardium 50 of the heart of the patient.

Such a system may further include a window configured for placement against skin of the patient, wherein the window is sized sufficiently to permit radiation to be emitted from the spectral probe 40 toward the myocardium 50 by one or more radiation sources, and to be received from the myocardium 50 to the spectral probe 40 by one or more detectors 80.

A system according to some embodiments of the present invention includes an electrode assembly 1100 including a sternum electrode 1102 coupled to an apex electrode 1104, and a spectral sensor 1108, which may also be referred to as spectral probe 40, coupled to the sternum and apex electrodes 1102, 1104 so as to be arranged over an intercostal space over a heart 52 of a patient when the sternum electrode 1102 is properly positioned on the right sternum and the apex electrode 1104 is properly positioned on the left torso, wherein the spectral sensor 1108 is configured to measure a physiologic parameter of a myocardium 50 of the heart of the patient.

A method for measuring a myocardial physiologic parameter according to an embodiment of the present invention includes placing an at least partially convex portion of a spectral probe 40 against an intercostal space of a human over a heart 52 of the human and measuring a physiologic parameter of a myocardium 50 of the heart with the spectral probe 40 over time during an emergency medical event. Such method may further include attaching the spectral sensor to the intercostal space with adhesive, and/or pressing the spectral sensor into the intercostal space, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for assisting sensor position on a patient, the system comprising:
    a probe comprising a plurality of sensors, the plurality of sensors comprising:
        one or more first sensors configured to generate first sensor data representing one or more physiologic parameters of a subject, and
        one or more second sensors configured to generate second sensor data representing a position of the probe;
    one or more indicators; and
    one or more processors communicably coupled to the plurality of sensors and the one or more indicators, wherein the one or more processors are configured to:
        while the probe is positioned at a first position on the subject, determine, based on the first sensor data, a first metric representing an effectiveness of the probe in determining the one or more physiologic parameters of the subject at the first position,
        while the probe is positioned at a second position on the subject, determine, based on the first sensor data, a second metric representing an effectiveness of the probe in determining the one or more physiologic parameters of the subject at the second position,
        compare the first metric and the second metric, and
        indicate, using the one or more indicators, a suggested position adjustment of the probe to the user based on the comparison and the second sensor data.

2. The system of claim 1, further comprising a patient monitor system comprising at least some of the one or more processors, wherein the probe is configured to be removably coupled to the patient monitor system.

3. The system of claim 1, wherein the first sensor data is indicative of a blood flow of the subject.

4. The system of claim 1, wherein the one or more first sensors comprise:
    one or more radiation sources, and
    one or more spectral detectors.

5. The system of claim 1, wherein the first sensor data represents at least one of:
    an SmO2 measurement associated with the subject,
    a pH measurement associated with the subject,
    a hematocrit measurement associated with the subject, or
    a CO2 measurement associated with the subject.

6. The system of claim 1, wherein the first sensor data comprises:
    a plurality of electrocardiogram (ECG) traces associated with the subject, and
    spectroscopic data associated with the subject.

7. The system of claim 6, wherein determining the first metric comprises:
    determining a first cross-correlation coefficient between (i) a first ECG trace obtained while the probe was positioned at the first position on the subject, and (ii) a first set of the spectroscopic data obtained while the probe was positioned at the first position on the subject.

8. The system of claim 7, wherein determining the second metric comprises:
    determining a second cross-correlation coefficient between (i) a second ECG trace obtained while the probe was positioned at the first position on the subject, and (ii) a second set of the spectroscopic data obtained while the probe was positioned at the second position on the subject.

9. The system of claim 8, wherein determining the second metric comprises:
    determining a difference between the second cross-correlation coefficient and the first cross-correlation coefficient.

10. The system of claim 1, wherein the one or more second sensors comprise at least one inertial sensor.

11. The system of claim 1, wherein the one or more second sensors comprise at least one accelerometer.

12. The system of claim 1, wherein the one or more second sensors comprise at least one gyroscope.

13. The system of claim 1, wherein the first sensor data represents at least one of:
    a rotational position of the probe, or
    a longitudinal position of the probe along the subject.

14. The system of claim 1, wherein indicating the suggested position adjustment of the probe to the user comprises:
    indicating a suggested direction of translation for the probe.

15. The system of claim 14, wherein indicating the suggested direction of translation for the probe comprises:
    presenting an arrow having the suggested direction of translation for the probe.

16. The system of claim 1, wherein indicating the suggested position adjustment of the probe to the user comprises:
    indicating a suggested rotation for the probe.

17. The system of claim 16, wherein indicating the suggested rotation for the probe comprises at least one of:
    indicating a suggested clockwise rotation of the probe using a first indicator of the one or more indicators, or
    indicating a suggested counterclockwise rotation of the probe using a second indicator of the one or more indicators different from the first indicator.

18. The system of claim 1, wherein the one or more indicators comprise one or more visual indicators.

19. The system of claim 1, wherein the one or more indicators comprise one or more audio feedback devices.

20. The system of claim 1, wherein the one or more indicators comprise one or more haptic feedback devices.

* * * * *